United States Patent [19]
Waldman et al.

[11] Patent Number: 5,868,732
[45] Date of Patent: Feb. 9, 1999

[54] COOLING APPARATUS FOR CUTANEOUS TREATMENT EMPLOYING A LASER AND METHOD FOR OPERATING SAME

[75] Inventors: Amir Waldman, Hod Hasharon; Michael Slatkine, Herzlia; Ofer Braude, Ramat Gan; Arie Klein, Kfar Saba; Yitzhak Rozenberg, Tel Aviv; Jerry Talpalariu, Petach Tikya, all of Israel

[73] Assignee: ESC Medical Systems, Ltd., Yokneam, Israel

[21] Appl. No.: 729,240

[22] Filed: Oct. 9, 1996

[30] Foreign Application Priority Data

May 12, 1996 [IL] Israel ......................................... 118229

[51] Int. Cl.$^6$ ..................................................... A61B 17/36
[52] U.S. Cl. ................................................................. 606/9
[58] Field of Search .................................. 606/1, 2, 4, 5, 606/6, 10, 11, 12, 14, 15, 16, 17

[56] References Cited

U.S. PATENT DOCUMENTS

| | | | |
|---|---|---|---|
| 5,133,708 | 7/1992 | Smith | 606/5 |
| 5,143,071 | 9/1992 | Keush et al. | 128/640 |
| 5,282,797 | 2/1994 | Chess | 606/9 |
| 5,336,217 | 8/1994 | Bays et al. | 606/9 |
| 5,368,590 | 11/1994 | Itoh | 606/4 |
| 5,486,172 | 1/1996 | Chess | 606/20 |
| 5,505,726 | 4/1996 | Meserol | 606/9 |
| 5,507,740 | 4/1996 | O'Donnell, Jr. | 606/4 |
| 5,595,568 | 1/1997 | Anderson et al. | 606/9 |
| 5,683,380 | 11/1997 | Eckhouse et al. | 606/9 |
| 5,741,245 | 4/1998 | Cozean et al. | 606/5 |

*Primary Examiner*—Max Hindenburg
*Assistant Examiner*—Sonya Harris-Ogugua
*Attorney, Agent, or Firm*—Richard I. Samuel, Esq.; Friedman Siegelbaum LLP

[57] ABSTRACT

Apparatus and method for tracking the operation of a light beam, preferably a laser light beam, which operates to treat the skin of the patient. The apparatus includes plurality of markings in accordance with the light beam impinges on the locations to be treated. The apparatus including the plurality of markings may be a cooling apparatus which also cools the skin during the treatment.

12 Claims, 4 Drawing Sheets

COOLING APPARATUS FOR CUTANEOUS TREATMENT EMPLOYING A LASER AND METHOD FOR OPERATING SAME

FIELD OF THE INVENTION

The present invention relates to laser based systems for cutaneous treatment generally and more particularly to a cooling apparatus having markings which enable to track the operation of a laser on the skin.

BACKGROUND OF THE INVENTION

Skin treatment employing laser based systems, usually pulsed laser based systems is well known in the art. Such laser based systems are used inter alia for cutaneous vascular lesions treatment and for hair removal, the latter application being described for example in U.S. Pat. Nos. 5,059,192 to Zaias and 5,226,907 to Tankovich.

As is also well known in the art, the operation of laser based systems for cutaneous treatment is more effective when the tissue is cooled. Examples for prior art devices for cooling the skin during laser treatment are U.S. Pat. No. 5,057,104, U.S. Pat. No. 5,282,797 and U.S. Pat. No. 5,486,172 to Chess specifically designed for cutaneous vascular lesions treatments and U.S. Pat. No. 5,344,418 to Ghaffari.

A major disadvantage of prior art laser based systems for cutaneous treatment is that the operation of the laser is not visible to the physician carrying the treatment, thus he can not be sure that the laser covered the entire area to be treated. This results in an inhomogeneous treatment of the skin, such as an inhomogeneous removal of hair from the patient skin in the case of hair removal treatment.

SUMMARY OF THE INVENTION

It is therefore an object of the present invention to enable a physician operating a laser for cutaneous treatment to track the laser beam operation.

Accordingly, the present invention provides an apparatus which includes a plurality of markings enabling a physician to track the laser operation.

It is a further object of the present invention to provide an improved cooling apparatus to be used in conjunction with laser beam cutaneous treatments.

According to an aspect of the invention, the apparatus can be part of a cooling apparatus operating to cool the area treated by the laser beam.

It is yet a further object of the present invention to provide an improved laser based system for cutaneous treatment.

There is thus provided, in accordance with a preferred embodiment of the present invention, an apparatus for providing a plurality of markings for tracking the operation of a laser beam on the skin of a patient substantially simultaneously with the operation of the laser beam thereupon.

Preferably, the plurality of markings indicate the locations on which the laser beam impinges. Additionally, the plurality of markings may be vaporized in response to impingement of a laser beam thereupon.

In a preferred embodiment, the plurality of markings are marked on a transparent sheet forming the apparatus, the sheet preferably formed of substantially of polyethylene or polycarbonate.

In a preferred embodiment, the plurality of markings are discrete dots or grid junctions.

There is also provided, in accordance with a preferred embodiment of the present invention a cooling apparatus for cooling the skin during treatment with a light source comprising an enclosure for enclosing a cooling substance therein, the enclosure having thereon a plurality of markings, the plurality of markings for tracking the operation of the light beam operating to treat an area of the skin of a patient.

In a preferred embodiment, the enclosure is a flexible enclosure preferably formed substantially of polyethylene or polycarbonate.

In operation, the plurality of markings indicate the locations on which the laser beam impinges. They may be vaporized in response to impingement of the laser beam thereupon.

According to a preferred embodiment of the present invention, the cooling substance is a gel and the enclosure has a peelable cover so as to enable direct contact between the gel and the area of the skin of a patient. Preferably, the edge of the enclosure exposed by peeling the peelable cover includes an adhesive material for attaching the cooling apparatus to the patient skin.

There is also provided, in accordance with a preferred embodiment of the present invention, a laser based system for treating the skin of a patient which includes a laser source operative to generate a laser beam and a cooling apparatus for cooling the skin of a patient substantially simultaneously with the operation of the laser beam, the cooling apparatus being the cooling apparatus of the present invention.

There is also provided, in accordance with a preferred embodiment of the present invention, a method for cutaneous treatment employing a light beam, preferably but not necessarily a laser light beam, which includes the steps of providing a plurality of markings indicating locations on which a light beam impinges during treatment of an area of the skin to be treated and impinging the light beam in accordance with individual ones of the plurality of markings, whereby effectively covering the area of the skin to be treated.

According to a preferred embodiment, the method includes the step of vaporizing each of the markings upon impingement of the light beam.

In one preferred embodiment, the step of providing includes the step of physically marking the plurality of markings on the area of the skin to be treated. In another preferred embodiment, an apparatus including the plurality of markings over the area of the skin to be treated is disposed intermediate the laser beam and the skin. In yet another embodiment, the step of providing includes the step of projecting the plurality of markings onto the area of the skin to be treated.

In accordance with a preferred embodiment of the present invention, the method also includes the step of cooling the area of the skin to be treated during the operation of the light beam. In one preferred embodiment, the area to be treated is cooled with a cooling apparatus attached to the area of the skin to be treated. In an alternative embodiment, a gel is spread on the area of the skin to be treated.

BRIEF DESCRIPTION OF THE DRAWINGS

The present invention will be understood and appreciated more fully from the following detailed description taken in conjunction with the appended drawings in which.

DESCRIPTION OF THE PREFERRED EMBODIMENTS

Figure 1A:
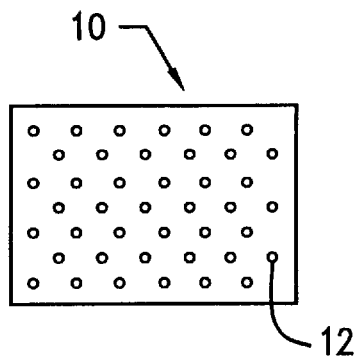
FIGS. 1A and 1B are schematic illustrations of an apparatus including a plurality of markings, constructed in accordance with two alternative embodiments of the present invention.
Figure 1B:
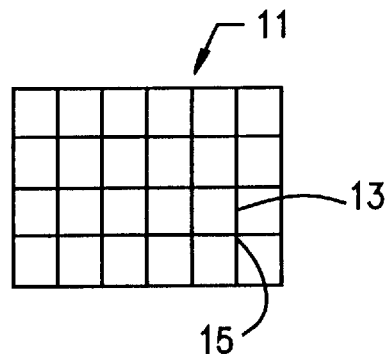

Reference is now made to FIGS. 1A and 1B which illustrate an apparatus having a plurality of markings thereon, the markings for tracking the operation of a laser beam operative to remove hairs from a patient skin and indicating whether the laser beam actually operated in a location on the skin corresponding to each marking.

The apparatus of FIG. 1A, generally referenced 10, comprises a plurality of markings 12 which are preferably, but not necessarily, ordered in generally similar distances therebetween. In the illustrated embodiment, markings 12 are black dots which vaporize in response to impinging of the laser beam thereupon. The apparatus of FIG. 1B, generally referenced 11, comprises a grid 13 wherein each grid junction 15 is operative similarly to dots 12.

In an alternative embodiment, the plurality of markings are not being vaporized by impingement of the laser beam thereupon.

In the embodiments of FIGS. 1A and 1B apparatus 10 and 11, respectively, are sheets of transparent material, such as polyethylene or polycarbonate and markings 12 and grid 13 is made of any suitable marking, such as ink printed on the polyethylene or the polycarbonate sheet. In a further embodiment of the present invention, apparatus 10 and 11 form part of a cooling apparatus as described in detail with reference to FIGS. 3 and 4 hereinbelow. In yet a further embodiment of the present invention, markings 12 are marked on the skin. In yet another embodiment, the markings are projected on the skin as illustrated with respect to FIG. 5 hereinbelow.

Figure 2A:
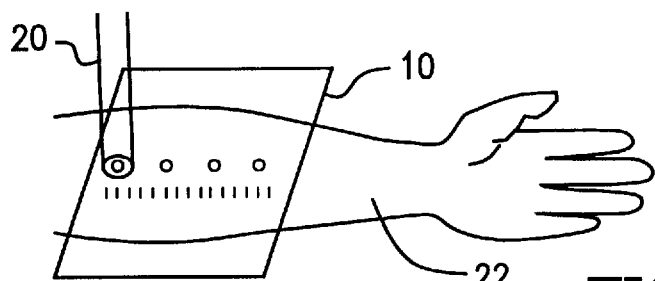
FIGS. 2A–2C are schematic pictorial illustrations of the operation of the apparatus of FIG. 1A.
Figure 2B:
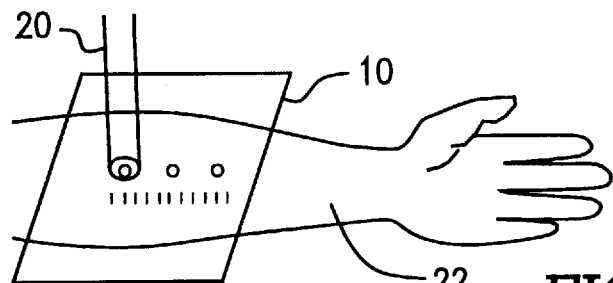
Figure 2C:
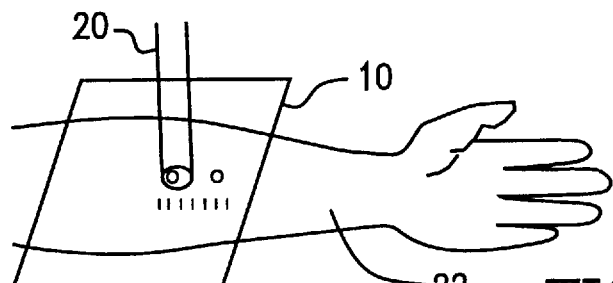

In operation, as illustrated in FIGS. 2A–2C to which reference is now made, apparatus 10 is placed intermediate laser source 20 and the hand 22 of a patient substantially parallel to the skin tissue. Laser source 20, preferably, but not necessarily, a hand held pulsed Ruby laser, Alexandrite laser or Nd-Yag laser apparatus with or without frequency doubler or quadrupler is moved by a physician over the hand 22 so as to progressively remove hairs therefrom. As illustrated in FIGS. 2A–2C which illustrate the progression of the treatment from t1 through t2 to t3, each laser pulse is directed to a marking 12 so as to vaporize the marking 12 and the hairs 24 thereunder. In the illustrated nonlimiting embodiment, with each pulse an additional marking 12 and the hairs 24 thereunder disappear. In an alternative embodiment, the dots 12 or the grid 13 are used to indicate the vicinity and not the exact location on which the laser beam impinges and therefore are not being vaporized by impingement of the laser beam thereupon.

By directing laser pulse 20 a desired number of times to all markings 12, substantially full coverage of the area to be treated is effectively covered.

Figure 3A:
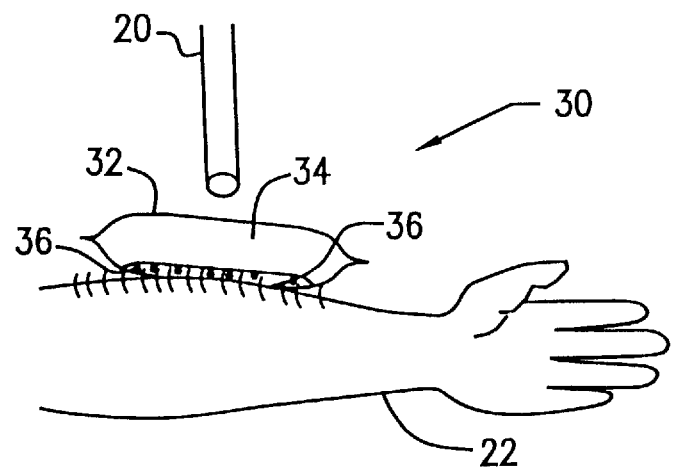
FIG. 3A is a schematic pictorial illustration of a cooling apparatus, constructed and operative in accordance with a preferred embodiment of the present invention.

Referring now to FIG. 3A, the apparatus 10 is illustrated as part of a cooling apparatus so as to further increase the effectiveness of the laser treatment. While the cooling apparatus may be any prior art cooling apparatus, in a preferred embodiment of the present invention the cooling apparatus, generally referenced 30 comprises a flexible enclosure 32 formed of a relatively thin plastic material, such as polyethylene, having therein any suitable cooling substance 34, a non limiting example being water preferably with salt to decrease its freezing temperature, and markings 36 which are operative similarly to markings 12. Alternatively, an apparatus similar to apparatus 10 or 11 is disposed in enclosure 32 as shown in FIG. 3B.

A particular feature of the present invention is the use of an ultrasound gel 38, such as the Aquarius 101 Ultrasound gel, commercially available from Meditab Ltd. of Israel. Gel 38 is disposed intermediate hand 22 and cooling apparatus 30. Since enclosure 32 is flexible it is more easy to handle and to place over hand 22 than prior art cooling apparatus. However, since enclosure 32 need not be necessarily in direct contact with the skin, gel 38 provides the required optical index matching between the skin and cooling apparatus 30.

Figure 3B:
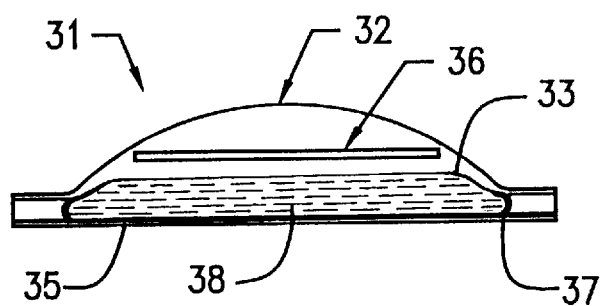
FIG. 3B is a schematic pictorial illustration of a cooling apparatus, constructed and operative in accordance with another preferred embodiment of the present invention.

According to an alternative preferred embodiment of the present invention illustrated in FIG. 3B to which reference is now made, a cooling apparatus, generally referenced 31 is provided. Cooling apparatus 31 is substantially similar to cooling apparatus 30 and therefore similar elements are referenced in FIGS. 3A and 3B by the same reference numerals. Cooling apparatus 31 differs from cooling apparatus 30 in that it also includes gel 38 enclosed therein in an enclosure 33 having peelable cover 35. In operation, peelable cover 35 is peeled and cooling apparatus 31 is attached to the skin with attachments 37. Preferably, the edge of the enclosure 33 exposed by peeling the peelable cover includes an adhesive material which serves as the attachment 37 for attaching the cooling apparatus to the patient skin.

Figure 4:
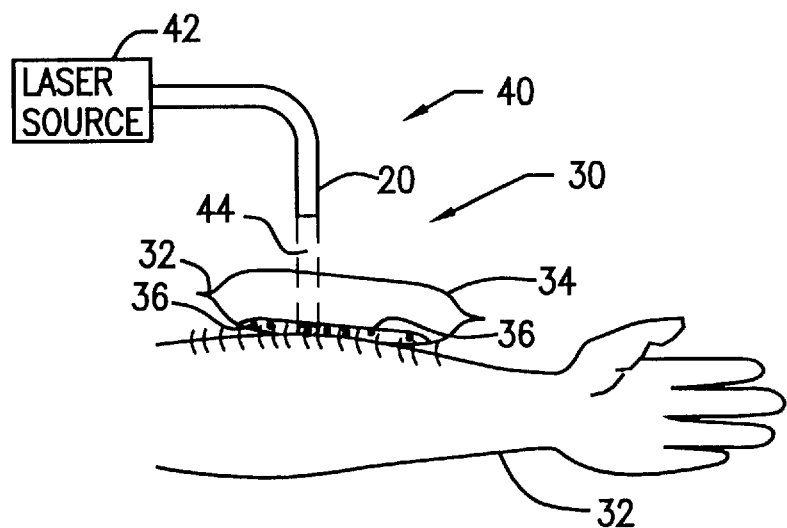
FIG. 4 is a schematic pictorial illustration of a system for hair removal, constructed and operative in accordance with a preferred embodiment of the present invention.

Cooling apparatus 30 and cooling apparatus 31 are used in conjunction with a laser based skin treatment system, generally referenced 40, illustrated in FIG. 4 to which reference is now made. It will be appreciated that while FIG. 4 is described with respect to cooling apparatus 30, it may equally be applied to operate with cooling apparatus 31.

System 40 includes a laser source 42, which refers herein to the entire laser apparatus operating to provide a pulsed laser beam 44 and only schematically shown, a cooling apparatus 30 and gel 38.

Laser source 42 may be any suitable laser source for skin treatment, such as a pulsed Ruby laser or Alexandrite laser.

In operation, gel 36 is spread over the area of the skin to be treated and cooling apparatus 30 is placed thereon intermediate gel 38 and laser source 42. A physician (not shown) then operated to treat the skin with the pulsed laser 44 as described hereinabove with reference to FIGS. 2A through 2C.

It will be appreciated that the preferred embodiments described hereinabove are described by way of example only and that numerous modifications thereto, all of which fall within the scope of the present invention, exist. A non-limiting example is that while the preferred embodiments have been described with respect to hair removal from a patient hand, the present invention is equally applicable to any other cutaneous treatment of any part of the patient body.

Figure 5:
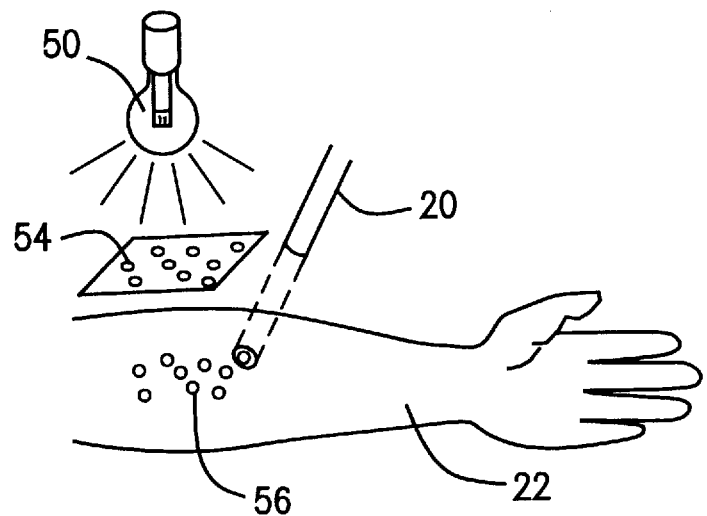
FIG. 5 is a schematic illustration of a marking projection system, constructed and operative in accordance with a preferred embodiment of the present invention.

Another example is that while the present invention has been described with respect to markings 12 it is equally applicable to grid 13. Yet another example is to employ a projection apparatus in order to project the markings on the treated area as illustrated in FIG. 5 to which reference is now made. In the embodiment of FIG. 5 a light source 50 projects light through a transparent sheet 52 having markings 54 thereon so as to effectively mark hand 22 with shade markings 56.

Figure 6A:
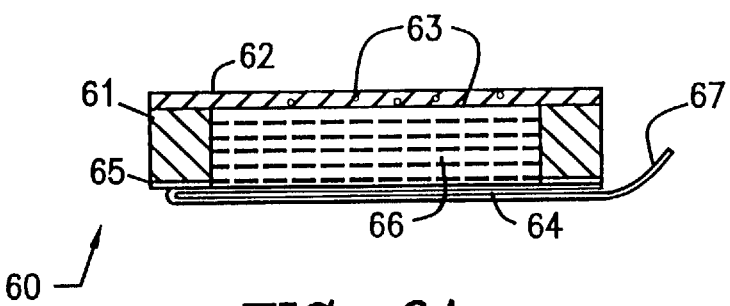
FIG. 6A is a schematic pictorial illustration of a cooling apparatus, constructed and operative in accordance with yet another preferred embodiment of the present invention.

Yet another example illustrated in FIG. 6 to which reference is now made is to use a cooling apparatus in which the markings are part of the enclosure and not of a marking disposed therein. The cooling apparatus of FIG. 6, generally referenced 60 comprises an enclosure 61 of which the top part 62 facing away from the skin during operation includes discrete marks 63 or a grid thereon and of which the bottom part is a folded removable cover 64 removed after apparatus 60 is attached to the skin employing attachments 65. Disposed in enclosure 61 is gel 66 used as the cooling agent during operation of the laser on the skin.

Figure 6B:
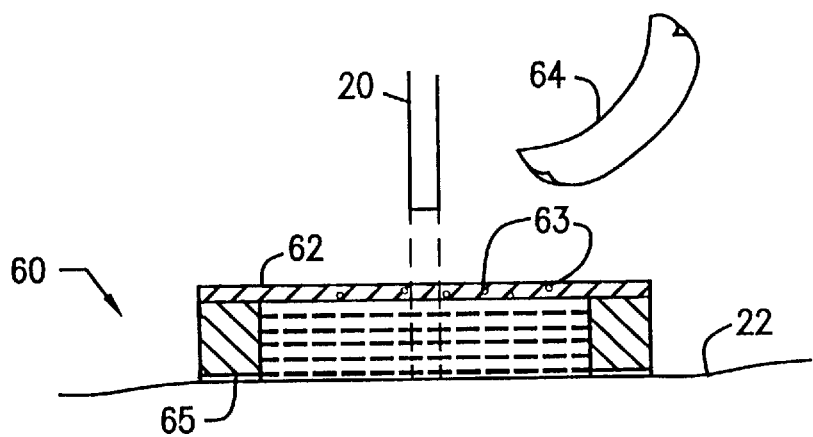
FIG. 6B illustrates the cooling apparatus of FIG. 6B in operation.

In operation, apparatus 60 is placed on the skin, peelable cover is pulled out by pulling its edge 67, gel 66 comes into contact with the area to be treated as shown in FIG. 6B and the laser beam 20 starts operation on the treated area in accordance with the plurality of markings 63.

In an alternative embodiment, he peelable cover 64 is removed before cooling apparatus 60 is tied to the skin.

While the foregoing description and drawings represent the preferred embodiments of the present invention, it will be understood that various changes and modifications may be made without departing from the spirit and scope of the present invention. For example, a colored marking at the edge of any cooling apparatus, such as cooling apparatus 60 may be added such that the cooling apparatus marks the area being treated.

It will also be appreciated that while the present invention has been described with respect to a laser any of the apparatus described hereinabove may operate in conjunction with an incoherent flash lamp source instead of a laser source.

It will also be appreciated by persons skilled in the art that the present invention is not limited by what has been particularly shown and described herein above. Rather the scope of the invention is defined by the claims which follow:

We claim:

1. A laser surgery apparatus, comprising:

a laser that generates at least one pulsed laser beam in a path;

a cooling substance arranged in said path to cool skin; and a plurality of markings arranged to provide an indication of where the pulsed laser beam passes through said cooling substance.

2. An apparatus as in claim 1, further comprising an envelope containing said cooling substance, said envelope being transparent and flexible.

3. An apparatus as in claim 1, wherein said markings vaporize in response to infringement by said pulsed laser beam.

4. An apparatus as in claim 1, further comprising a projector that projects light to shine through a transparent sheet having any one of dots and grid junctions whose shade corresponds to the markings.

5. An apparatus as in claim 1, wherein said markings are arranged within said path.

6. An apparatus as in claim 1, wherein said markings are arranged outside the path but in a vicinity to allow the indication to be made.

7. A method of performing laser surgery, comprising the steps of:

generating at least one pulsed laser beam in a path;

cooling the skin by arranging a cooling substance in said path; and arranging a plurality of markings that provide an indication of where the pulsed laser beam passes through said cooling substance.

8. A method as in claim 7, further comprising the step of flexing an envelope that contains the cooling substance, the envelope being transparent.

9. A method as in claim 7, wherein said markings vaporize in response to infringement by said pulsed laser beam.

10. A method as in claim 7, wherein the step of arranging includes projecting the markings with a light source shining through a transparent sheet having any one of dots and grid junctions whose shade corresponds to the markings.

11. A method as in claim 7, wherein said markings are arranged within the path.

12. A method as in claim 7, wherein said markings are arranged outside the path but in a vicinity to allow the indication to be made.

* * * * *